United States Patent [19]

Coles

[11] 4,351,842
[45] Sep. 28, 1982

[54] N-CYCLOPROPYLISOINDOLINES

[75] Inventor: Richard J. Coles, Uxbridge, England

[73] Assignee: Glaxo Laboratories Limited, Greenford, England

[21] Appl. No.: 170,929

[22] Filed: Jul. 21, 1980

Related U.S. Application Data

[63] Continuation of Ser. No. 897,047, Apr. 17, 1978, abandoned.

[30] Foreign Application Priority Data

Apr. 26, 1977 [GB] United Kingdom ............... 17305/77

[51] Int. Cl.$^3$ .................. A61K 31/40; C07D 209/44; C07D 209/46; C07D 209/60
[52] U.S. Cl. ..................................... 424/274; 560/51; 560/80; 562/462; 568/808; 570/183; 570/185; 549/236; 549/240; 548/421; 548/427; 548/450; 548/469; 548/470
[58] Field of Search ..................... 260/326.1; 424/274

[56] References Cited

U.S. PATENT DOCUMENTS

| | | | |
|---|---|---|---|
| 2,740,795 | 4/1956 | Wenner | 260/326.1 |
| 3,897,452 | 7/1975 | Anderson et al. | 260/326.1 |
| 3,996,373 | 12/1976 | Blattner | 260/326.1 |
| 4,052,508 | 10/1977 | Anderson et al. | 260/326.1 |
| 4,088,772 | 5/1978 | Ciganek | 260/326.1 |

FOREIGN PATENT DOCUMENTS

| | | | |
|---|---|---|---|
| 827087 | 3/1974 | Belgium | 260/326.1 |
| 31901 | 5/1965 | German Democratic Rep. | 260/326.1 |

Primary Examiner—Alton D. Rollins
Attorney, Agent, or Firm—Bacon & Thomas

[57] ABSTRACT

Compounds of the general formula:

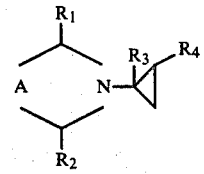

in which
A is a benzene ring or a carbocyclic aromatic group consisting of two or three fused benzene rings, the group A being linked to the nitrogen containing ring at two adjacent carbon atoms and the benzene ring or each benzene ring optionally carrying one or more substituents which may be the same or different, and may be alkyl, aryl, halo, hydroxy, acyloxy or alkoxy, or two adjacent positions in a ring may be substituted so as to form a methylene dioxy group (—O—CH$_2$—O—);
$R_1$ and $R_2$ which may be the same or different, each represent hydrogen; an alkyl group which contains 1 to 6 carbon atoms and which may be substituted; a hydroxycarbonyl or an alkoxycarbonyl group; and
one of $R_3$ and $R_4$ represents hydrogen, an alkyl group which contains 1 to 6 carbon atoms and which may be substituted, or a hydroxy, alkoxy, hydroxycarbonyl or alkoxycarbonyl group and the other of $R_3$ and $R_4$ represents hydrogen, or a non-toxic physiologically acceptable salt or bioprecursor thereof.

These compounds are useful in the treatment of patients suffering from depression.

34 Claims, No Drawings

N-CYCLOPROPYLISOINDOLINES

This is a continuation of application Ser. No. 897,047, filed Apr. 17, 1978, now abandoned.

This invention relates to novel isoindoline derivatives, to processes for the preparation thereof, and to pharmaceutical compositions containing them as well as to their use in medicine.

We have found that compounds of formula I below and their non-toxic physiologically acceptable salts possess central nervous system, in particular anti-depressant activity.

According to the invention therefore there are provided novel isoindoline derivatives of the formula I:

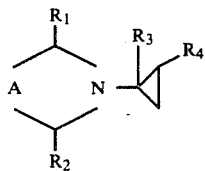

(I)

in which
A is a benzene ring or a carbocyclic aromatic group consisting of two or three fused benzene rings, the group A being linked to the nitrogen containing ring at two adjacent carbon atoms. Each benzene ring may optionally carry one or more substituents, which may be the same or different, and may be alkyl, aryl, halo, hydroxy, acyloxy or alkoxy, or two adjacent positions in a ring may be substituted so as to form a methylene dioxy group (—O—CH$_2$—O—).

$R_1$ and $R_2$ may be the same or different, each represent hydrogen, or an alkyl, hydroxycarbonyl or alkoxycarbonyl group. The alkyl groups may be substituted by for example, hydroxy, acyloxy, alkoxy, halo, alkylamino or dialkylamino;

and one of $R_3$ and $R_4$ represents hydrogen, alkyl, hydroxy, alkoxy, hydroxycarbonyl or alkoxycarbonyl.

The other of $R_3$ and $R_4$ represents hydrogen.

The alkyl groups may be substituted as defined above for $R_1$ and $R_2$.

In the above definition, alkyl groups either as such or part of a group contain 1–6, and preferably 1–4, carbon atoms. The terms "alkoxy" and "acyloxy", either as applied to a substituent group or part of a substituent group, preferably mean such a group containing 1–6, and advantageously 1–4, carbon atoms. The term "acyloxy" also extends to aroyloxy. Aryl preferably means phenyl. A is preferably benzene, naphthalene, anthracene or phenanthrene.

Preferred compounds of formula I are those in which:
$R_1$ is hydrogen, alkyl such as methyl, ethyl or n-propyl, hydroxyalkyl such as hydroxymethyl, alkoxycarbonyl such as ethoxycarbonyl or dialkylaminoalkyl such as diethylaminomethyl; and $R_2$ is hydrogen, alkyl such as methyl or ethyl or hydroxyalkyl such as hydroxymethyl.

Of the substituents $R_3$ and $R_4$, one of these is hydrogen and the other is preferably hydrogen, alkyl such as methyl or ethyl, alkoxy such as n-butoxy, hydroxyalkyl such as hydroxymethyl, or alkoxyalkyl such as methoxymethyl.

Preferred substituents in the carbocyclic aromatic ring or rings of group A other than hydrogen are halogen, particularly chlorine or fluorine; alkyl, particularly methyl; aryl, particularly phenyl; alkoxy, particularly methoxy; hydroxy; or methylenedioxy.

Preferably the group A contains no substituents other than hydrogen or contains only one such substituent, which is preferably hydroxy, alkoxy or halo. Preferably $R_1$ and $R_2$ are both hydrogen or one may be alkyl and the other hydrogen. Preferably $R_3$ and $R_4$ are both hydrogen or $R_3$ is alkyl, hydroxyalkyl, alkoxyalkyl or acyloxyalkyl, with $R_4$ as hydrogen.

A is most advantageously benzene or naphthalene. In the latter case, two possibilities exist, namely 2,3-dihydro-1H-naphth[2',3'-d]azol-2-ines more commonly called benz[f]isoindolines (structure IA below), and 2,3-dihydro-1H-naphth[1',2'-d]azol-2-ines more commonly called benz[e]-isoindolines (structure IB below)

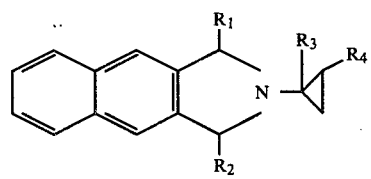

(IA)

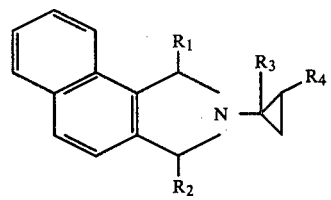

(IB)

In the benz[e]isoindoline series $R_1$ and $R_2$ are preferably hydrogen, and the benzene rings of the naphthalene moiety are preferably unsubstituted.

The following compounds are particularly preferred; 2-(1'-hydroxymethylcyclopropyl)benz[e]isoindoline and its hydrochloride; 2-cyclopropyl-5-hydroxyisoindoline; 2-cyclopropyl-6-methoxy-2,3-dihydro-1H-naphth[2',3'-d]-azol-2-ine; 2-(1'-methoxymethylcyclopropyl)benz[f]isoindline; 2-cyclopropyl-1-ethylbenz[f]isoindoline; 2-(1'-methylcyclopropyl)-6-fluoro-2,3-dihydro-1H-naphth[2',3'-d]-azol-2-ine; 2-cyclopropylisoindoline; 6-chloro-2-cyclopropyl-2,3-dihydro-1H-naphth[2',3'-d]azol-2-ine; 6-fluoro-2-cyclopropyl-2,3-dihydro-1H-naphth[2',3'-d]azol-2-ine; 2-(1'-methylcyclopropyl)benz[f]isoindoline and 2-cyclopropyl-4-fluoroisoindoline.

In general, when $R_1$–$R_4$ are not all hydrogen, geometrical and/or optical isomerism may exist. The invention extends to the new compounds defined in whatever isomeric form.

The compounds according to the invention may form salts and non-toxic physiologically acceptable salts, in particular acid addition salts, are within the scope of the invention. Such salts include those of inorganic acids, such as hydrochlorides and sulphates and those of organic acids such as acetates and tartrates. Bioprecursors and hydrates are also within the scope of the invention.

As mentioned above, the compounds of the invention show inter alia an anti-depressant effect. The test used for determining their activity is the anti-tetrabenazine test, carried out on mice.

This test is based on that described by Vernier, V. G., Hanson, H. M. and Stone, C. A. in "Psychosomatic Medicine" (Ed. J. H. Nodine and J. H. Moyer) pp 683-90. Lea and Febiger, Philadephia 1962.

Administration of tetrabenazine results in depletion of brain amines and consequent depression of the central nervous system. This is reflected by changes in the animal such as ptosis, hypothermia and catalepsy, some or all of which may be prevented by prior administration of a compound having anti-depressant activity.

The compounds of the invention have a marked anti-depressant effect. In certain compounds this is associated with reduced side effects when compared with known anti-depressants.

The compounds according to the invention may be made by a number of processes.

In one process an intermediate of formula II:

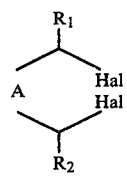

(in which Hal represents halogen which may be the same or different and $R_1$ and $R_2$ are as defined above or groups convertible thereto) may be reacted with an optionally substituted cyclopropylamine of formula III:

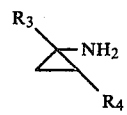

(in which $R_3$ and $R_4$ represent the possible substituents in the cyclopropyl ring as defined above or groups convertible thereto). The reaction may conveniently be carried out in an organic solvent such as dioxan or chloroform at a temperature of from ambient to the reflux temperature of the reaction mixture, preferably in the presence of a base, for example an excess of the amine, an added tertiary amine such as triethylamine or an alkali metal carbonate, which base acts as an acid binding agent.

An alternative method of preparing compounds of the invention where $R_1$ and $R_2$ are hydrogen and $R_3$ and $R_4$ are both hydrogen or one is hydrogen and the other is alkyl or hydroxymethyl, involves reaction of an anhydride IV:

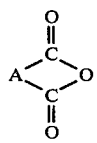

with a cyclopropylamine of formula III above in which $R_3$ and $R_4$ are both hydrogen or one is hydrogen and the other alkyl, hydroxymethyl or alkoxycarbonyl to give an imide of formula V:

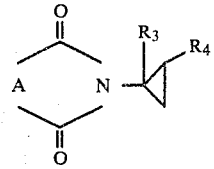

The imide (V) can then be reduced, for example with a complex metal hydride e.g. lithium aluminium hydride in a solvent such as tetrahydrofuran or ether at a temperature of from ambient to the reflux temperature of the mixture. This reduction will convert an alkoxycarbonyl group to a hydroxymethyl group. The reaction is preferably effected in two stages by reacting the components at ambient temperature and subjecting the resulting intermediate product to pyrolysis at above approximately 200° C. in an inert atmosphere.

The imides of formula V are novel and form part of the invention.

Compounds of formula I according to the invention may also be prepared by conversion of one compound of formula I of the invention into another compound of formula I of the invention, in particular by modification of substituent groups within the meanings given above. Thus, where one or more of $R_1$-$R_4$ is an alkoxycarbonyl group, this may for example be converted to a hydroxymethyl group by reduction with lithium aluminium hydride as described above for $R_3$ and $R_4$. In another case where one of $R_1$-$R_4$ is hydroxymethyl, this may be converted into for example a chloromethyl group, which may then be reacted with a primary or secondary alkylamine.

A hydroxyalkyl group may also be converted to an alkoxyalkyl or acyloxyalkyl group by alkylation or acylation by conventional methods. Thus, a hydroxymethyl group may be alkylated for example with dimethyl sulphate to give a methoxymethyl group. Also a hydroxymethyl group may be acylated, e.g. with acetyl chloride, to give an acetoxymethyl group.

Substituents in the benzene rings when present may be present in the starting materials. However when the substituent is a hydroxy group this may be protected, and the protecting group may be removed at any suitable stage in the reaction sequence. Where the substituent is alkoxy this may be converted to a hydroxy group, for example by reaction with boron tribromide in an inert solvent, e.g. a halocarbon or benzene solvent.

The intermediate of formula II specified above in which $R_1$ and $R_2$ are hydrogen or alkoxycarbonyl may be prepared by standard methods such as halogenation of a compound of formula VI:

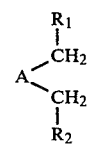

using a halogenating agent such as N-bromosuccinimide.

A further method of making compounds of formula II where $R_1$ and $R_2$ are hydrogen is by reduction of an anhydride of formula IV above followed by halogenation with a halogenating agent such as thionyl chloride.

A further method for the preparation of compounds of formula II in which $R_1$ and $R_2$ are the same and are alkyl comprises treating compounds of the formula VII:

with a suitable organometallic reagent such as a Grignard reagent $R_1 MgX$ where X is halogen and $R_1$ is alkyl followed by treatment with a hydrogen halide in a halocarbon solvent e.g. hydrogen bromide in methylene chloride.

A further method for preparation of the dihalo intermediates of formula II, in which $R_1$ is a group $CH_2R_5$ where $R_5$ is hydrogen or alkyl and $R_2$ is hydrogen, involves the treatment of the anhydride of formula IV with malonic acid or a suitably substituted malonic acid to give a keto carboxylic acid derivative VIII, as indicated in the following reaction scheme.

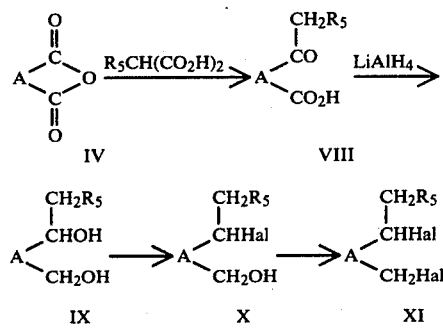

Reduction of VIII with lithium aluminium hydride then gives the corresponding dihydroxy compound IX which is subsequently halogenated to XI. The final step halogenation takes place in one or two stages and can thus produce a dihalo product corresponding to formula II above in which the two halogen atoms are either the same or different. The first stage requires the use of a hydrogen halide in a halocarbon solvent.

The compounds of the invention may be formulated in association with pharmaceutical non-toxic carriers or diluents and may be presented in liquid, solid or semiliquid form, for administration, and the invention extends to such pharmaceutical compositions.

Preferably the compositions are presented in a form suitable for oral administration, i.e. in the form of tablets, capsules or the like or as granules formulated with a sweetening agent such as sucrose and a flavouring agent, said granules being reconstitutable with water if desired, or as a syrup. In particular they are preferably presented in a form of a dosage unit, advantageously in the form of a tablet or capsule, containing an amount of the active ingredient within the range of 5–100 mg per dosage unit when used for their effect on the central nervous system. The pharmaceutical compositions may contain other active ingredients.

The following Examples (in which temperatures are in °C.) and preparations illustrate the invention:

EXAMPLE 1

2-Cyclopropylbenz[f]isoindoline hydrochloride

Cyclopropylamine (10 g) in dioxan (50 ml) was added to 2,3-bis(bromomethyl)naphthalene (15.6 g) in dioxan (300 ml) over 1 hr. The precipitate which formed was filtered and the filtrate was evaporated to dryness. The residue was partitioned between aqueous sodium hydroxide and ether and the ethereal layer was extracted with aqueous hydrochloric acid. The resultant slurry was combined with the aqueous extract and then evaporated to dryness to give a residue which was recrystallised from iso-propanol to give 2-cyclopropylbenz[f]isoindoline hydrochloride (3.9 g, m.p. 210°).

The compounds specified in Table 1 below were prepared in a similar manner from the starting materials indicated. Solvents used for recrystallisation are indicated in brackets.

TABLE 1

| Example No | | | |
|---|---|---|---|
| 2 | 1,2-Bis(bromomethyl)naphthalene 9g. | Cyclopropylamine 9g | 2-Cyclopropylbenz[e]isoindoline hydrochloride 2.0g., m.p. 227° (iso-propanol/ethyl acetate) |
| 3 | 1,2-Bis(chloromethyl)benzene 9g. | Cyclopropylamine 8g | 2-Cyclopropylisoindoline hydrochloride 3.0g., m.p. 168° (iso-propanol/ethyl acetate). |
| 4 | 1-Chloro-2,3-bis(bromoethyl)naphthalene 3.5g. | Cyclopropylamine 4g. | 4-Chloro-2-cyclopropylbenz[f]isoindoline hydrochloride 0.5g., m.p. 222° (water). |
| 5 | 6-Chloro-2,3-bis(chloromethyl)naphthalene 8.6g. | Cyclopropylamine 8g. | 6-Chloro-2-cyclopropyl-2,3-dihydro-1H-naphth[2',3'-d]azol-2-ine hydrochloride 1.6g., m.p. >300° (iso-propanol/water). |
| 6 | 6-Methyl-2,3-bis(chloromethyl)naphthalene 4.0g. | Cyclopropylamine 4g. | 6-Methyl-2-cyclopropyl-2,3-dihydro-napth[2',3'-d]azol-2-ine hydrochloride 0.5g., m.p. 191° (iso-propanol/ethyl acetate). |
| 7 | 6-Fluoro-2,3-bis(chloromethyl)naphthalene 2.5g. | Cyclopropylamine 5g. | 6-Fluoro-2-cyclopropyl-2,3-dihydro-1H-naphth[2',3'-d]azol-2-ine hydrochloride 0.75g., m.p. 223° (iso-propanol). |
| 8 | 4,5-Methylenedioxy-1,2-bis(chloromethyl)benzene 9.0g. | Cyclopropylamine 9g. | 2-Cyclopropyl-5,6-methylenedioxy isoindoline hydrochloride 1.6g., m.p. 232° (dec). (iso-propanol/water). |
| 9 | 4-Methoxy-1,2-bis(bromomethyl)benzene 8.0g. | Cyclopropylamine 9g. | 2-Cyclopropyl-5-methoxyisoindoline hydrochloride 2.0g., m.p. 204° (isopropanol/ethyl acetate). |
| 10 | 2,3-Bis(1'-bromoethyl)naphthalene* 7g. [Preparation 1(i)] | Cyclopropylamine 8g. | 2-Cyclopropyl-1,3-dimethylbenz[f]isoindoline hydrochloride 3g., m.p. 210° (iso-propanol/ethyl acetate). |

TABLE 1-continued

| Example No | | | |
|---|---|---|---|
| 11 | 2,3-Bis(1'-bromopropyl)naphthalene* 6g. [Preparation 1(ii)] | Cyclopropylamine 6g. | 2-Cyclopropyl-1,3-diethylbenz[f]-isoindoline hydrochloride 1.0g., m.p. 198° (iso-propanol/ethyl acetate). |
| 12 | 1,2-Bis(1'-bromoethyl)benzene* 4g. [Preparation 1(iii)] | Cyclopropylamine 4g. | 2-Cyclopropyl-1,3-dimethylisoindoline hydrochloride 1.1g., m.p. 186° (iso-propanol/ethyl acetate). |
| 13 | 2,3-Bis(bromomethyl)naphthalene 6g. | 1-methylcyclopropyl-amine 6g. | 2-(1'-Methylcyclopropyl)benz[f]isoindoline hydrochloride 1.5g., m.p. 176° (iso-propanol/ethyl acetate). |
| 14 | 1,2-Bis(bromomethyl)benzene 5g. | 1-methylcyclopropyl-amine 5g. | 2-(1'-Methylcyclopropyl)isoindoline hydrochloride 1.7g., m.p. 158° (iso-propanol/ethyl acetate). |
| 15 | 2,3-Bis(bromomethyl)naphthalene 4g. | 2-methylcyclopropyl-amine 3g. | 2-(2'-Methylcyclopropyl)benz[f]isoindoline hydrochloride 0.55g., m.p. 212° (iso-propanol/ethyl acetate). |
| 16 | 1,2-Bis(bromomethyl)benzene 7g. | 2-methylcyclopropyl-amine 6g. | 2-(2'-Methylcyclopropyl)isoindoline hydrochloride 1.10g., m.p. 153° (iso-propanol/ethyl acetate) (a) |
| 17 | 2,3-Bis(bromomethyl)naphthalene 3g. | 2-n-Butoxycyclopropyl-amine 2g. | 2-(2'-n-butoxycyclopropyl)benz[f]isoindoline hydrochloride 0.3g., m.p. 184° (iso-propanol/ethyl acetate). |
| 18 | 2-Bromomethyl-3-(1'-bromoethyl)naphthalene* 8g. [Preparation 3(ii)] | Cyclopropylamine 20g. | 2-Cyclopropyl-1-methylbenz[f]isoindoline hydrochloride 3.9g., m.p. 219° (iso-propanol/ethyl acetate). |
| 19 | 1-Chloromethyl-2-(1'-bromoethyl)-benzene* 9g. [Preparation 4(i)] | Cyclopropylamine 11g | 2-Cyclopropyl-1-methylisoindoline hydrochloride 3.4g., m.p. 202° (isopropanol/ethyl acetate). |
| 20 | 2-Bromomethyl-3-(1'-bromopropyl)-naphthalene* 7g [Preparation 3(i)] | Cyclopropylamine 8g | 2-Cyclopropyl-1-ethylbenz[f]-isoindoline hydrochloride 1.6g., m.p. 179° (iso-propanol/ethyl acetate). |
| 21 | 1-Chloromethyl-2-(1'-bromopropyl)-benzene* 11g. [Preparation 4(ii)] | Cyclopropylamine 12g | 2-Cyclopropyl-1-ethylisoindoline hydrochloride 0.4g., m.p. 164° (iso-propanol/ethyl acetate). |
| 22 | 2-Bromomethyl-3-(1'-bromoethyl)-naphthalene* 7g [Preparation 3(ii)] | 1-methylcyclopropyl-amine 5g. | 2-(1'-Methylcyclopropyl)-1-methylbenz[f]isoindoline hydrochloride 0.6g., m.p. 216° (iso-propanol/ethyl acetate). |
| 23 | 1-Bromomethyl-2-(1'-bromo-1'-ethoxycarbonylmethyl)benzene* 3.4g. [Preparation 2(i)] | Cyclopropylamine 4g. | 2-Cyclopropyl-1-ethoxycarbonyl-isoindoline hydrochloride 1.5g., m.p. 148° (iso-propanol/ethyl acetate). |
| 24 | 2-Bromomethyl-3-(1'-bromobutyl)-naphthalene* 10g. [Preparation 3(iii)] | Cyclopropylamine 7g. | 2-Cyclopropyl-1-n-propylbenz[f]isoindoline hydrochloride 3.9g., m.p. 215° (Aqueous hydrochloric acid). |
| 25 | 5-Chloro-2,3-bis(chloromethyl)-naphthalene 3.0g. | 1-Methylcyclopropyl-amine 3.0g. | 5-Chloro-2-(1'-methylcyclopropyl)-2,3-dihydro-1H-naphth[2',3'-d]azol-2-ine hydrochloride 0.3g., m.p. 210° (iso-propanol/ethyl acetate). |
| 26 | 2,3-Bis(bromomethyl)naphthalene 8g. | 2-Ethylcyclopropyl-amine* 6g. [Preparation 8] | 2-(2'-Ethylcyclopropyl)benz[f]isoindoline hydrochloride 0.5g., m.p. 206° (iso-propanol/ethyl acetate). |
| 27 | 1,2-Bis(bromomethyl)naphthalene 6g. | 1-Methylcyclopropyl-amine 4g. | 2-(1'-Methylcyclopropyl)benz[e]isoindoline hydrochloride 1.7g., m.p. 190° (iso-propanol/ethyl acetate). |

*The preparations of these compounds are described below, the appropriate Preparation No. having been given in brackets.
(a) In a similar experiment the initial product was chromatographed [diethylamine/cyclohexane (1:6) eluent; silica support] to give the constituent isomers as free bases (both oils) which were reconverted to their hydrochloride salts [cis. m.p. 158° (iso-propanol/ethyl acetate), trans m.p. 168° (iso-propanol/ethyl acetate)].

EXAMPLE 28

4-Phenyl-2-cyclopropylbenz[f]isoindoline hydrochloride

1-Phenyl-2,3-naphthalenedicarboxylic anhydride (3.0 g) and cyclopropylamine (5 ml) were shaken for 5 minutes. The reaction mixture became very warm and excess cyclopropylamine was evaporated in vacuo. The solid remaining was then heated at 220° to 240° for 5 minutes in a nitrogen atmosphere. The solid formed was allowed to cool and was recrystallised from light petroleum (b.p. 40°–60°)/chloroform to give 2-cyclopropyl-1,3-dioxo-4-phenylbenz[f]isoindoline, (2.7 g, m.p. 198°).

The foregoing solid (2.0 g) was added to lithium aluminium hydride (1.5 g) in THF (100 ml) over 2 hr. and the reaction was left overnight at room temperature. Water was added, the resultant slurry was washed with diethylether (4×100 ml), the ethereal washings were dried, filtered and extracted with aqueous hydrochloric acid. The resultant slurry was combined with the aqueous extract which was when evaporated to dryness to give a residue which was recrystallised from isopropanol/ethyl acetate (charcoal) to give 4-phenyl- 2-cyclopropylbenz[f]isoindoline hydrochloride (0.9 g., m.p. 207°).

The compounds specified in Table 2 were prepared similarly from the starting materials indicated.

TABLE 2

| Example No | | | |
|---|---|---|---|
| 29 | 6-Methoxy-2,3-naphthalene dicarboxylic anhydride 2.5g. | 2-Cyclopropyl-6-methoxy-2,3-dihydro-1,3-dioxo-1H-naphth-[2',3'-d]azol-2-ine m.p. 182° | 2-Cyclopropyl-6-methoxy-2,3-dihydro-1H-naphth[2',3'-d]-azol-2-ine hydrochloride 1.5g., m.p. 198° (dec.) (iso-propanol/ethyl acetate). |
| 30 | 5-Chloro-2,3-naphthalene dicarboxylic anhydride 3.0g. | 2-Cyclopropyl-5-chloro-2,3-dihydro-1,3-dioxo-1H-naphth-[2',3'-d]azol-2-ine m.p. 183° | 2-Cyclopropyl-5-chloro-2,3-dihydro-1H-naphth[2',3'-d]-azol-2-ine hydrochloride 1.5g., m.p. 205° (iso-propanol/ethyl acetate]. |
| 31 | 4-Chlorophthalic anhydride 6.0g. | 2-Cyclopropyl-5-chloro-1,3-dioxoisoindoline m.p. 103° | 2-Cyclopropyl-5-chloro-isoindoline hydrochloride 2.5g., m.p. 194° (iso-propanol/ethyl acetate). |
| 32 | 6-Hydroxy-2,3-naphthalene dicarboxylic anhydride* 1.5g. [Preparation 5] | 2-Cyclopropyl-6-hydroxy-2,3-dihydro-1,3-dioxo-1H-naphth-[2',3'-d]-azol-2-ine m.p. 252° | 2-Cycloproyl-6-hydroxy-2,3-dihydro-1H-naphth[2',3'-d]-azol-2-ine 0.45g. mp 207° (Acetone). |
| 33 | 4-Methylphthalic anhydride 1.0g. | 2-Cyclopropyl-5-methyl-1,3-dioxoisoindoline m.p. 78° | 2-Cyclopropyl-5-methyl isoindoline hydrochloride (a) 1.2g., m.p. 174°. |
| 34 | | 2-(1'-Ethoxycarbonylcyclopropyl)-1,3-dioxo-4-fluoro-isoindoline* 2.0g. [Preparation 6] | 2-(1'-Hydroxymethylcyclopropyl)-4-fluoroisoindoline hydrochloride (a) 0.45g., m.p. 130° |
| 35 | 3-Fluorophthalic anhydride 5g. | 2-Cyclopropyl-1,3-dioxo-4-fluoroisoindoline m.p. 101° | 2-Cyclopropyl-4-fluoroisoindoline b.p. 70°/1 mm., hydrochloride (a) 0.32g., m.p. 180° dec. |
| 36 | 3-Fluorophthalic anhydride 1.5g. | 2-(1'-Methylcyclopropyl)-1,3-dioxo-4-fluoroisoindoline m.p. 114° | 2-(1'-Methylcyclopropyl)-4-fluoroisoindoline 0.45g., b.p. 88°/1 mm., hydrochloride (a) m.p. 142° |
| 37 | 6-Fluoro-2,3-naphthalene dicarboxylic anhydride 1.4g. | 2-(1'-Methylcyclopropyl)-6-fluoro-1,3-dioxo-2,3-dihydro-1H-naphth[2',3'-d] azol-2-ine m.p. 192° | 2-(1'-Methylcyclopropyl)-6-fluoro-2,3-dihydro-1H-naphth[2',3'-d]azol-2-ine hydrochloride (a) 0.65g., m.p. 158° |
| 38 | 3-Fluorophthalic anhydride 1.5g. | 4-Fluoro-2-(2'-methylcyclopropyl)-1,3-dioxoisoidoline (oil) | 2-(2'-Methylcyclopropyl)-4-fluoro isoindoline hydrochloride (a) 0.8g., m.p. 178° |
| 39 | 4-Chlorophthalic anhydride 6.0g. | 5-Chloro-2-(2'-methylcyclopropyl)-1,3-dioxoisoindoline m.p. 108° | 5-Chloro-2-(2'-methylcyclopropyl) isoindoline hydrochloride (a) 0.9g., m.p. 156° |
| 40 | Anthracene-2,3-dicarboxylic anhydride 3g. | 2-Cyclopropyl-1,3-dioxo-2,3-dihydro-1H-anthr[2',3'-d] azol-2-ine m.p. 305° | 2-Cyclopropyl-2,3-dihydro-1H-anthr[2',3'-d]azol-2-ine 0.17g., m.p. 235–237° (Dimethylformamide). |

*The preparation of these compounds is described below.
(a) Product isolated from an ethereal solution of the free base treated with ethereal hydrogen chloride, filtered and dried in vacuo immediately.

EXAMPLE 41

2-Cyclopropyl-5-hydroxyisoindoline

Boron tribromide (24 g) was added dropwise to 2-cyclopropyl-5-methoxyisoindoline (4.2 g) in dichloromethane (100 ml) kept at −78°. The solution was allowed to warm to room temperature overnight and then poured carefully onto ice/water (400 ml).

The aqueous phase was evaporated to dryness and diethylamine was added to the residue. The resultant solution was evaporated to dryness and the residual oil was extracted with ethyl acetate. The organic extracts were evaporated to dryness and the residue was recrystallised from acetone to give 2-cyclopropyl-5-hydroxyisoindoline, (0.7 g., m.p. 170°).

EXAMPLE 42

2-Cyclopropyl-1-hydroxymethylisoindoline hydrochloride

2-Cyclopropyl-1-ethoxycarbonylisoindoline (13 g) in THF (20 ml) was added to lithium aluminium hydride (5.4 g) in THF (150 ml) over 15 min. The reaction mixture was stirred for 2 hr. and water was added. The resultant slurry was washed with ether (5×150 ml), the ethereal washings were dried (magnesium sulphate) and evaporated to dryness. The residue (5.8 g) was dissolved in ether and extracted with aqueous hydrochloric acid, the acid extract was evaporated to dryness and a portion of the residue was recrystallised from iso-propanol/ethyl acetate to give 2-cyclopropyl-1-hydroxymethylisoindoline hydrochloride (0.85 g., m.p. 163°).

The compounds specified in Table 3 were prepared in a similar manner from the starting materials indicated.

TABLE 3

| Example No. | STARTING MATERIALS | PRODUCTS |
|---|---|---|
| 43 | 2-(1'-Ethoxycarbonylcyclopropyl)benz[f]-isoindoline 1.4g. | 2-(1'-Hydroxymethylcyclopropyl)benz[f]-isoindoline hydrochloride 0.90g., m.p. |

TABLE 3-continued

| Example No. | STARTING MATERIALS | PRODUCTS |
| --- | --- | --- |
| | | 208° (Ethanol/ethyl acetate) |
| 44 | 2-(1'-ethoxycarbonylcyclopropyl)-isoindoline 0.8g. | 2-(1'-Hydroxymethylcyclopropyl)isoindoline hydrochloride 0.50g., m.p. 98° (Iso-propanol/ethyl acetate). |
| 45 | 2-Cyclopropyl-1,3-bis(ethoxycarbonyl)-benz[f]isoindoline 1.5g. (m.p. 60°, Preparation 7) | 2-Cyclopropyl-1,3-bis(hydroxymethyl)benz[f]-isoindoline 0.6g., m.p. 151° (Light petroleum (b.p. 40–60°)/dichloromethane). (Isomer I.) |
| 46 | 2-Cyclopropyl-1,3-bis(ethoxycarbonyl)benz-[f]-isoindoline 1.9g. (oil, Preparation 7) | 2-Cyclopropyl-1,3-bis(hydroxymethyl)benz[f]-isoindoline 1.5g., m.p. 152° (Light petroleum (b.p. 40–60°)/dichloromethane). (Isomer II). |

EXAMPLE 47

2-Cyclopropyl-1-diethylaminoethylisoindoline dihydrochloride

2-Cyclopropyl-1-hydroxymethylisoindoline (3.8 g) was stirred with thionyl chloride (35 ml) for 3 hr. Thionyl chloride was evaporated to give crude 2-cyclopropyl-1-chloromethylisoindoline (as an oil) which was dissolved in chloroform (50 ml) and treated with diethylamine (15 ml). The reaction mixture was left for 12 hr, evaporated to dryness and the residue was partitioned between aqueous sodium hydroxide and ether. The ether layer was washed (water), evaporated to dryness in vacuo, and the residue was redissolved in ether and extracted with aqueous hydrochloric acid. The acidic extract was evaporated to dryness and the residue was recrystallised from iso-propanol/ethyl acetate to give 2-cyclopropyl-1-diethylaminomethylisoindoline dihydrochloride, (0.35 g, m.p. 150°).

EXAMPLE 48

2-(1'-Methoxymethylcyclopropyl)benz[f]isoindoline hydrochloride

A mixture of 2-(1'-hydroxymethylcyclopropyl)-benz[f]-isoindoline (2.4 g), 60% sodium hydroxide (10 ml), benzene (40 ml) and benzyltriethylammonium chloride (0.2 g) was vigorously stirred whilst dimethylsulphate (1.50 g) was added at a temperature below 30°. The reaction mixture was stirred for a further 24 hr., diluted with water (50 ml) and filtered. The benzene layer was dried (magnesium sulphate) and evaporated to dryness; the residue was dissolved in ether and mixed with ethereal hydrogen chloride. The precipitate was filtered and recrystallised from iso-propanol/ethyl acetate to give 2-(1'-methoxymethylcyclopropyl)benz[f]isoindoline hydrochloride (0.13 g, m.p. 158°).

EXAMPLE 49

2-(1'-Hydroxymethylcyclopropyl)benz[e]isoindoline hydrochloride

Ethyl 1-aminocyclopropanecarboxylate hydrochloride (16 g) in chloroform (50 ml) was added to 1,2-bis(-bromomethyl)naphthalene (40 g) and potassium carbonate (40 g) in chloroform (200 ml) kept at 60°. The reaction mixture was refluxed for a further 6 hr and then filtered; the filtrate was evaporated to dryness and the residue [i.e. crude 2-(1'-carbethoxycyclopropyl)benz-[e]isoindoline] was dissolved in THF (150 ml) and added to lithium aluminium hydride (10 g) in THF (100 ml) over 0.5 h. Water was then added and the resultant slurry was filtered and the filtrate was evaporated to dryness; the residue was partitioned between ether and water and the ether layer was extracted with concentrated hydrochloric acid. The acidic extract was evaporated to dryness to give a residue which was recrystallised from iso-propanol/ethyl acetate to give the title compound (5.9 g. m.p.192°).

PREPARATION 1

(i) 2,3-Bis(1'-bromoethyl)naphthalene

A solution of 2,-bis(1'-hydroxyethyl)naphthalene (7.0 g) in dichloromethane (100 ml) was saturated with hydrogen bromide gas. The solution was stirred for 2 hr. and volatile materials were evaporated in vacuo at room temperature; the residual 2,3-bis(1'-bromoethyl)-naphthalene was used immediately without further purification.

Similarly prepared (as oils) were (ii) 2,3-bis(1'-bromopropyl)naphthalene [from 2,3-bis(1'-hydroxypropyl)-naphthalene] and (iii) 1,2-bis(1'-bromoethyl)benzene [from 1,2-bis(1'-hydroxyethyl)-benzene].

2,3-Bis(1'-hydroxypropyl)naphthalene was prepared from 2,3-naphthalenedicarboxaldehyde and ethyl magnesium bromide.

PREPARATION 2

(i) 1-Bromomethyl-2-(1'-bromo-1'-ethoxycarbonylmethyl)benzene

The title compound (isolated as an oil) was prepared by the method described by G. Cignarella, F. Savelli and P. Sanna (Synthesis, 1975, 252) for the analogous methoxycarbonyl compound.

(ii) 2,3-Bis(1'-bromo-1'-ethoxycarbonylmethyl)naphthalene (isolated as an oil) was prepared by the method described by G. Cignarella et al (same reference as in (i) above) for 1,2-bis(1'-bromo-1'-methoxycarbonylmethyl)benzene.

PREPARATION 3

(i) 2-Bromomethyl-3-(1'-bromopropyl)naphthalene

A mixture of 2,3-naphthalenedicarboxylic anhydride (35.5 g), methylmalonic acid (25 g) and triethylamine (250 ml) was stirred and refluxed for 8 hr. The cooled reaction mixture was poured onto 10% hydrochloric acid (2 liter) and the aqueous slurry was extracted with chloroform (1.5 liter). The dried (magnesium sulphate) extract was evaporated to dryness to give an oil which was recrystallised from light petroleum (b.p. 60°–80°)/chloroform to give 3-(1'-oxopropyl)naphthalene-2-carboxylic acid (23 g, m.p. 147°).

The above carboxylic acid (11 g) in THF (150 ml) was added to lithium aluminium hydride (6.0 g) in THF (150 ml) over 0.5 hr. The reaction mixture was stirred for 2 hr. and water was carefully added. The resultant slurry was washed with ether (3×100 ml) and the combined ethereal washings were dried (magnesium sulphate) and evaporated to dryness to give 2-hydroxymethyl-3-(1'-hydroxypropyl)naphthalene as an oil; a small portion was recrystallised from light petroleum (b.p. 60°-80°)/chloroform to give a crystalline solid, m.p. 70°.

The foregoing oil (9.5 g) was dissolved in dichloromethane (200 ml) and the solution was saturated with hydrogen bromide gas. The solution was stirred for 2 hr. and volatile materials were evaporated in vacuo. The residual 2-bromomethyl-3-(1'-bromopropyl)naphthalene was used immediately; a small portion was recrystallised from acetone to give a crystalline solid, m.p. 104°-107°. In a similar manner:

(ii) Replacement of methylmalonic acid by malonic acid in the above sequence gave 3-(1'-oxoethyl)naphthalene-2-carboxylic acid (m.p. 145°), 2-hydroxymethyl-3-(1'-hydroxyethyl)naphthalene (oil) and thence 2-bromoethyl-3-(1'-bromoethyl)naphthalene (oil). (iii) Replacement by ethylmalonic acid gave 3-(1'-oxobutyl)naphthalene-2-carboxylic acid (m.p. 109°), 2-hydroxymethyl-3-(1'-hydroxybutyl)naphthalene (oil) and thence 2-bromoethyl-3-(1'-bromobutyl)naphthalene (oil).

PREPARATION 4

(i) 1-Chloromethyl-2-(1'-bromoethyl)benzene (a) (i) Using the method of Preparation 3, phthalic anhydride and malonic acid gave 2-(1'-oxoethyl)benzoic acid (m.p. 110°) and thence 1-hydroxymethyl-2-(1'-hydroxyethyl)benzene (oil)

(ii) Similarly prepared from phthalic anhydride and methylmalonic acid were 2-(1'-oxopropyl)benzoic acid and thence 1-hydroxymethyl-2-(1'-hydroxypropyl)benzene (both as oils). (b) (i) 1-Hydroxymethyl-2-(1'-hydroxyethyl)benzene (10 g) was dissolved in dichloromethane (200 ml) and was saturated with hydrogen bromide gas. The solution was stirred for 2 hr. and volatile materials were evaporated to give 1-hydroxymethyl-2-(1'-bromoethyl)-benzene as an oil. Thionyl chloride (30 ml) was added to the oil and the solution was stirred for 1 hr; evaporation of thionyl chloride gave 1-chloromethyl-2-(1'-bromoethyl)benzene which was used immediately. (ii) Similarly prepared from 1-hydroxymethyl-2-(1'-hydroxypropyl)benzene were 1-hydroxymethyl-2-(1'-bromopropyl)benzene and thence 1-chloromethyl-2-(1'-bromopropyl)benzene (both as oils).

PREPARATION 5

6-Hydroxy-2,3-naphthalenedicarboxylic anhydride

6-Methoxy-2,3-naphthalenedicarboxylic anhydride (4.0 g) and pyridine hydrochloride (8.0 g) were fused at 240° for 0.5 hr. in a nitrogen atmosphere. The flask contents were cooled, washed (water) and filtered to give a crude sample of 6-hydroxy-2,3-naphthalenedicarboxylic anhydride (m.p. 266°) which was used without purification.

PREPARATION 6

2-(1'-Ethoxycarbonylcyclopropyl)-1,3-dioxo-4-fluoroisoindoline

3-Fluorophthalic anhydride (2.0 g), ethyl 1-aminocyclopropane carboxylate hydrochloride (4.0 g) and triethylamine (4 ml) were stirred in chloroform (30 ml) for 0.5 h. Volatile material was evaporated and the residue was heated at 210° for 0.25 h in a nitrogen atmosphere; the residue was dissolved in THF (insoluble triethylame hydrochloride was discarded) and the ethereal solution was evaporated to dryness. This residue was recrystallised from dichloromethane/light petroleum (40°-60°) to give the title compound m.p. 164°.

PREPARATION 7

2-Cyclopropyl-1,3-bis(ethoxycarbonyl)benz[f]isoindoline 2,3-Bis(1'-bromo-1'-ethoxycarbonylmethyl)-naphthalene (10.0 g) [Preparation 2(ii)] in chloroform (150 ml) was treated with cyclopropylamine (8.0 g) over 0. 25 h; the reaction mixture was left overnight and was then evaporated to dryness. The residue was purified by preparative t.l.c. (chloroform eluent, silica support) to give the two geometric isomers of 2-cyclopropyl-1,3-bis(ethoxycarbonyl)benz[f]isoindoline {isomer I, 2.9 g, m.p. 60° [light petroleum (40°-60°)/dichloromethane] and isomer II, 1.9 g (crude oil, not recrystallised)}.

PREPARATION 8

2-Ethylcyclopropylamine hydrochloride

2-Ethylcyclopropanecarboxylic acid (20 g) (b.p. 116°/20 mm., prepared from butylene oxide, triethylphosphonoacetate and sodium hydride in the manner described by N. C. Deno et al., *J. Amer. Chem. Soc,*, 1970, 92, 3700 for the preparation of 2-methylcyclopropanecarboxylic acid from propylene oxide) and thionyl chloride (22 g) were heated in chloroform (50 ml) for 12 h at 60°. The reaction mixture was distilled to give 2-ethylcyclopropanecarbonyl chloride (14.5 g, b.p. 156°-158°) which was dissolved in acetone (100 ml), cooled to −10° and treated with sodium azide (14 g) in water (35 ml). The reaction mixture was stirred at −10° for a further 0.5 h and was then poured onto ice/water, extracted with ether and the dried (magnesium sulphate) extract was cautiously evaporated to dryness at room temperature in vacuo. The residue was dissolved in toluene (100 ml) and carefully warmed to 100° and when the initial effervescence had subsided the solution was vigorously stirred at 100° for 1 h. Concentrated hydrochloric acid (50 ml) was added and the reaction mixture was refluxed for 15 min. with vigorous stirring. The acidic layer was evaporated to dryness and the residual oil (10 g) (2-ethylcyclopropylamine hydrochloride) was used without further purification.

Pharmaceutical Compositions

EXAMPLE 50

| Formula (per tablet) | |
| --- | --- |
| Active ingredient | 50.0 mg |
| Lactose | 105.0 mg |
| Maize starch | 40.0 mg |
| Polyvinyl pyrrolidone | 4.0 mg |
| Magnesium stearate | 1.0 mg |
| Tablet weight | 200.0 mg |

Method

Blend the active constituent with a portion of the lactose. Screen through 60 mesh sieve. Blend this with the remaining lactose and maize starch. Granulate the blend with alcoholic solution of polyvinyl pyrrolidone.

Pass granulate through a No 16 screen or mechanical granulator.

Dry granule at 40° C. and pass through a No 20 screen.

Blend the magnesium stearate with the granules and compress on tablet machine fitted with 8 mm diameter punches.

Filmcoat the tablets by intermittent or continuous spray methods using acceptable film forming materials and colouring matter.

EXAMPLE 51

Press-coated tablet

| Tablet Core | |
|---|---|
| Active ingredient | 50.0 mg |
| Lactose | 29.0 mg |
| Maize starch | 20.0 mg |
| Magnesium stearate | 1.0 mg |
| | 100.0 mg |
| Tablet coating | |
| Lactose | 196.25 mg |
| Maize starch | 50.00 mg |
| Dispersed (lake) colour | 1.25 mg |
| Magnesium stearate | 2.50 mg |
| | 250.0 mg |
| Total Tablet weight | 350.0 mg |

Method

Core granule

Blend active constituent with lactose and part of maize starch, screen 60 mesh, re-blend. Granulate with starch mucilage prepared with remaining starch. Screen 16 mesh. Dry in hot air oven at 50° C. Screen 20 mesh. Blend with lubricant.

Coating granules

Blend colour with small portion of lactose, screen 60 mesh. Blend with remaining lactose and part of starch by granual dilution. Granulate with starch mucilage prepared with remaining starch. Screen 12 mesh. Dry at 50° C. Screen 16 mesh. Blend with lubricant.

Compress tablets on Manesty Dry-Cota machine fitted with 6.5 mm diameter punches on core (LH) side and 10.00 mm diameter punches on coating (RH) side.

EXAMPLE 52

Hard gelatin capsule

| Active ingredient | 50.0 mg |
|---|---|
| Explotab | 4.0 mg |
| Lactose, anhydrous | 145.0 mg |
| Magnesium stearate | 1.0 mg |
| Capsule fill weight | 200.0 mg |

Method

Blend lubricant, Explotab with portion of lactose. Screen 60 mesh. Blend this with the active constituent. Screen 60 mesh. Add remaining lactose, blend and fill into lock-fit 2 piece hard gelatin capsules using an automatic or semi-automatic capsule filling machine (eg Zanasi). Capsule size depends on volume of blend.

What is claimed is:

1. A compound of the formula:

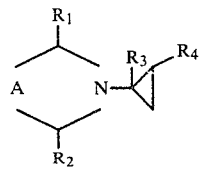

in which

A is a benzene ring or a carbocyclic aromatic group consisting of two benzene rings, the group A being linked to the nitrogen containing ring at two adjacent carbon atoms and the benzene ring or each benzene ring is unsubstituted or substituted by one or more substituents which may be the same or different, and are selected from the group consisting of alkyl containing 1–6 carbon atoms, phenyl, halogen, hydroxy, alkanoyloxy containing 1–6 carbon atoms in the alkanoyl portion or benzoyloxy, alkoxy containing 1–6 carbon atoms and a methylene dioxy group (O—CH$_2$—O—) which is connected to two adjacent positions in a ring;

$R_1$ and $R_2$ which may be the same or different, each represent hydrogen; an alkyl group which contains 1–6 carbon atoms and which is unsubstituted or substituted by hydroxy, alkanoyloxy containing 1–6 carbon atoms in the alkanoyl portion or benzoyloxy, alkoxy containing 1–6 carbon atoms, halogen, an alkylamino or dialkylamino group wherein the alkyl contains 1–6 carbon atoms; a hydroxycarbonyl or an alkoxycarbonyl group wherein the alkoxy contains 1–6 carbon atoms; and one of $R_3$ and $R_4$ represents hydrogen, an alkyl group which contains 1–6 carbon atoms, and which is unsubstituted or substituted by hydroxy, alkanoyloxy containing 1–6 carbon atoms in the alkanoyl portion or benzoyloxy, alkoxy containing 1–6 carbon atoms, halogen, an alkylamino or dialkylamino group wherein the alkyl contains 1–6 carbon atoms; hydroxy, alkoxy, hydroxycarbonyl or alkoxycarbonyl group wherein each alkoxy contains 1–6 carbon atoms and the other $R_3$ and $R_4$ represents hydrogen, or a non-toxic physiologically acceptable salt, or hydrate thereof.

2. The compound as defined in claim 1 wherein A is a benzene ring.

3. The compound as defined in claim 1 wherein A is a carbocyclic aromatic group consisting of two benzene rings.

4. The compound as defined in claim 3 wherein the two benzene rings form a benz[e] isoindoline.

5. The compound as defined in claim 3 wherein $R_1$ and $R_2$ are hydrogen and the benzene rings are unsubstituted.

6. The compound as defined in claim 3 wherein the two benzene rings form a benz[f] isoindoline.

7. A compound as claimed in claim 1 in which any of the groups $R_1$ to $R_4$ or a substituent on A is an alkyl group which contains 1–4 carbon atoms.

8. A compound as claimed in claim 1 in which any of the groups $R_3$ or $R_4$ or a substituent on A is an alkoxy group which contains 1–6 carbon atoms.

9. A compound as claimed in claim 1 in which a substituent on A is an alkanoyloxy group which contains 1–6 carbon atoms in the alkanoyl portion or benzoyloxy.

10. A compound as claimed in claim 1 in which any of the groups $R_1$ to $R_4$ is an alkyl group which is substituted by hydroxy, alkanoyloxy containing 1–6 carbon atoms in the alkanoyl portion or benzoyloxy; alkoxy, halo, alkylamino or dialkylamino.

11. A compound as claimed in claim 1 in which any of the substituents on A is a phenyl group.

12. A compound as claimed in claim 1 in which A is benzene, or naphthalene.

13. A compound as claimed in claim 1 in which $R_1$ is hydrogen, alkyl, hydroxyalkyl, alkoxycarbonyl or dialkylaminoalkyl; $R_2$ is hydrogen, alkyl or hydroxyalkyl, one of the groups $R_3$ and $R_4$ is hydrogen, alkyl, alkoxy, hydroxyalkyl or alkoxyalkyl, and the other is hydrogen, and the substituents on A other than hydrogen, are halogen, alkyl, phenyl, alkoxy, hydroxy or methylenedioxy.

14. A compound as claimed in claim 1 in which $R_1$ and $R_2$ are both hydrogen, or one is alkyl and the other hydrogen; $R_3$ and $R_4$ are both hydrogen or $R_3$ is alkyl, hydroxyalkyl, alkoxyalkyl, alkanoyloxy containing 1–6 carbon atoms in the alkanoyl portion or benzoyloxy, and $R_4$ is hydrogen and A contains no substituents other than hydrogen, or contains one such substituent which is hydroxy, alkoxy or halo.

15. The compound as claimed in claim 14 wherein $R_3$ is alkyl, hydroxyalkyl, alkoxyalkyl, alkanoyloxy containing 1–6 carbon atoms in the alkanoyl portion or benzoyloxy and $R_4$ is hydrogen.

16. A compound as claimed in claim 1 which is 2-cyclopropyl-isoindoline.

17. A compound as claimed in claim 1 which is 2-cyclopropyl benz[e] isoindoline.

18. A compound as claimed in claim 1 which is 2-cyclopropyl benz[f] isoindoline.

19. A compound as claimed in claim 1 which is 2-(1'-hydroxymethylcyclopropyl) benz[e] isoindoline or its hydrochloride.

20. A compound as claimed in claim 1 which is 2-cyclopropyl-5-hydroxyisoindoline.

21. A compound as claimed in claim 1 which is 2-cyclopropyl-6-methoxy-2,3-dihydro-1H-naphth[2',3-d]-azol-2-ine.

22. A compound as claimed in claim 1 which is 2-(1'-methoxymethylcyclopropyl) benz[f] isoindoline.

23. A compound as claimed in claim 1 which is 2-cyclopropyl-1-ethylbenz[f] isoindoline.

24. A compound as claimed in claim 1 which is 2-(1'-methylcyclopropyl)-6-fluoro-2,3-dihydro-1H-naphth[2',3'-d]azol-1-ine.

25. A compound as claimed in claim 1 which is 2-cyclopropylisoindoline.

26. A compound as claimed in claim 1 which is 6-chloro-2-cyclopropyl-2,3-dihydro-1H-naphth[2',3'-d]azol-2-ine.

27. A compound as claimed in claim 1 which is 6-fluoro-2-cyclopropyl-2,3-dihydro-1H-naphth[2',3'-d]azol-2-ine.

28. A compound as claimed in claim 1 which is 2-(1'-methylcyclopropyl)benz[f] isoindoline.

29. A compound as claimed in claim 1 which is 2-cyclopropyl-4-fluoro-isoindoline.

30. A pharmaceutical preparation containing as active ingredient an effective amount of a compound as claimed in claim 1 having anti-depressant activity in admixture with a pharmaceutically acceptable non-toxic carrier of diluent.

31. A pharmaceutical preparation as claimed in claim 30 in unit dosage form.

32. A pharmaceutical preparation as claimed in claim 31 which contains from 5 to 100 mg of active ingredient.

33. A pharmaceutical preparation as claimed in claim 30 which is in the form of tablets or capsules, or as granules formulated with a sweetening agent.

34. A method of treatment of a patient suffering from depression which comprises administering to the patient an effective amount of a compound as claimed in claim 1.

* * * * *